US008917389B2

(12) United States Patent
Piorek et al.

(10) Patent No.: US 8,917,389 B2
(45) Date of Patent: Dec. 23, 2014

(54) SERS DEVICES FOR THE REMOTE ANALYSIS OF ANALYTES

(75) Inventors: Brian D. Piorek, Santa Barbara, CA (US); Carl D. Meinhart, Santa Barbara, CA (US); Seung Joon Lee, Santa Barbara, CA (US)

(73) Assignee: OndaVia, Inc., Hayward, CA (US)

( * ) Notice: Subject to any disclaimer, the term of this patent is extended or adjusted under 35 U.S.C. 154(b) by 0 days.

(21) Appl. No.: 13/511,960

(22) PCT Filed: Nov. 29, 2010

(86) PCT No.: PCT/US2010/058234
§ 371 (c)(1),
(2), (4) Date: Sep. 19, 2012

(87) PCT Pub. No.: WO2011/066512
PCT Pub. Date: Jun. 3, 2011

(65) Prior Publication Data
US 2013/0003056 A1    Jan. 3, 2013

Related U.S. Application Data

(60) Provisional application No. 61/265,319, filed on Nov. 30, 2009.

(51) Int. Cl.
*G01J 3/44* (2006.01)
*G01N 21/65* (2006.01)
*G01N 21/17* (2006.01)

(52) U.S. Cl.
CPC ...... *G01N 21/658* (2013.01); *G01N 2021/1793* (2013.01); *G01N 2201/0221* (2013.01)
USPC .......................................................... 356/301

(58) Field of Classification Search
USPC ................................................ 356/301, 72–73
See application file for complete search history.

(56) References Cited

U.S. PATENT DOCUMENTS

| 4,781,458 A | 11/1988 | Angel et al. |
| 7,133,129 B2 * | 11/2006 | Lee et al. ...................... 356/301 |
| 7,403,281 B2 | 7/2008 | Carron et al. |
| 2003/0166297 A1 | 9/2003 | Natan |
| 2003/0231304 A1 | 12/2003 | Chan et al. |
| 2005/0024634 A1 * | 2/2005 | Barker et al. ................. 356/301 |
| 2008/0074662 A1 | 3/2008 | Gu |

OTHER PUBLICATIONS

International search report and written opinion dated Aug. 5, 2011 for PCT/US2010/058234.

* cited by examiner

*Primary Examiner* — Abdullahi Nur
(74) *Attorney, Agent, or Firm* — NUPAT, LLC

(57) ABSTRACT

SERS-active materials are delivered to a remote zone, then optically interrogated to detect and analyze from a safe distance the presence of explosives or other materials which may or may not be hazardous. Delivery methods include deploying projectiles comprising SERS-active material(s) which distribute their contents upon deployment to a target zone.

3 Claims, 2 Drawing Sheets

SERS DEVICES FOR THE REMOTE ANALYSIS OF ANALYTES

CROSS-REFERENCE

This application is filed pursuant to 35 U.S.C. §371 as a United States National Phase Application of International Application Ser. No. PCT/US10/058,234, filed Nov. 29, 2010, which claims the benefit of U.S. Provisional Application No. 61/265,319, filed Nov. 30, 2009, all of which are incorporated herein by reference in their entirety.

FIELD OF INVENTION

The invention relates to capturing airborne chemical species in the gas phase. More particularly, the invention relates to detection and/or analysis of low concentration chemical species using a SERS-active nanostructure(s).

BACKGROUND

Low concentrations of chemical species (analytes) targeted for detection and analysis pose unique technical challenges. Because low-concentration detection and analysis of some chemical compounds necessitate large and heavy lab apparatus, field deployment is often rendered difficult or impossible. In addition, the targeted analytes may be hazardous (e.g., toxic, explosive, or the like).

There is a need for apparatus and processes that are both field portable and accurate, offering accurate and repeatable detection/analysis of the targeted analyte(s) from a safe distance. Applications include chemical detectors (e.g., handheld chemical detectors or automated chemical detectors) for low-concentration analytes such as drugs, explosives, chemical and/or biological agents and weapons used in terrorist activities, and biological metabolites.

SUMMARY OF INVENTION

The invention provides systems and processes suitable for analyzing and/or detecting airborne or gas-phase analytes. Various aspects of the invention described herein may be applied to any of the particular applications set forth below or for other types of SERS-based analyte detection devices and systems. The invention may be applied as a stand-alone system or method, or as part of an integrated solution, such as a portable analyte detection system. It shall be understood that different aspects of the invention can be appreciated individually, collectively, or in combination with each other.

In some embodiments, systems or devices described herein include hand-held chemical detectors for low-concentration analytes, such as those derived from drugs, explosives, and biological systems, which are operable from a safe distance. In certain embodiments, provided herein is a mechanism or process for delivering SERS active sites (e.g., SERS active surfaces of SERS active materials suspended in a liquid and/or a volume of air); and analyzing the SERS active sites (e.g., SERS active surfaces of SERS active materials) with a Raman spectrometer (e.g., a Raman spectrometer which is at an area removed from the analyzed region to which the SERS active sites have been delivered).

In some embodiments, provided herein is an analyte detection system suitable for the detection of low volatility molecules, the system comprising
 a. a delivery mechanism or device for deploying a SERS-active sites or a deployable composition comprising SERS-active sites (e.g., providing a plurality of nanostructures comprising a SERS-active surface to a targeted or test zone, area or region); and
 b. a Raman spectrometer, optionally integrated with telescopic optics, configured to allow interrogation of the SERS-active surface of the SERS-active material (e.g., nanostructures comprising a SERS-active surface) or an analyte adsorbed thereon.

In certain embodiments, provided herein is an analyte detection system suitable for the detection of low volatility molecules, the system comprising a. a deployable composition comprising a SERS-active material (e.g., a plurality of nanostructures comprising a SERS-active surface);

b. an optional device for deploying the deployable composition to a location to be analyzed; and c. a Raman spectrometer, optionally integrated with telescopic optics, configured to allow interrogation of the SERS-active surface of the SERS-active material (e.g., nanostructures comprising a SERS-active surface) or an analyte adsorbed thereon.

In further embodiments, provided herein is a process for analyzing (e.g., detecting the presence of or measuring the amount of) volatility molecules, the process comprising:

a. deploying SERS-active sites or compositions comprising SERS-active sites to a targeted location; and b. remotely interrogating the SERS-active sites with a Raman spectrometer, optionally with an integrated telescopic optics, configured to allow interrogation of the SERS-active sites (e.g., SERS-active surface of SERS-active material) or an analyte adsorbed thereon.

In certain embodiments, the deployable composition is any composition suitable for being deployed to a remote location in a manner so as to allow an amount of SERS-active material (or the analytes adsorbed thereon) to be interrogated by a Raman spectrometer suitably located so as to observe the deployed composition. In certain embodiments, the Raman spectrometer may be integrated with telescopic optics. In some embodiments, the deployable composition may be in the form of a projectile, such as a solid projectile. In other embodiments, the deployable composition is a stream of SERS active sites suspended in liquid. In other embodiments the deployable composition is a liquid projectile.

In certain embodiments, the solid projectile is a fragmentable projectile. In certain instances, the fragmentable projectile fragments upon deployment thereby dispersing the enclosed SERS-active materials (e.g., nanostructures comprising SERS-active materials). In some embodiments, upon dispersion of the fragmentable projectile, at least a portion of the SERS-active materials (e.g., nanostructures comprising SERS-active materials) are rendered airborne. In certain embodiments, the Raman spectrometer is then utilized to interrogate the SERS-active surface of the airborne SERS-active materials (e.g., nanostructures comprising SERS-active materials). In some embodiments, upon dispersion of the fragmentable projectile, at least a portion of the SERS-active materials (e.g., nanostructures comprising SERS-active materials) are deposited upon a fixed surface. In certain embodiments, the Raman spectrometer is then utilized to interrogate the SERS-active surface of surface-deposited SERS-active materials (e.g., nanostructures comprising SERS-active materials).

In some embodiments, the solid projectile comprises SERS-active materials (e.g., nanostructures comprising SERS-active materials) and a solid carrier. In certain embodiments, the solid carrier is useful for protecting the nanostructures comprising SERS-active materials from contaminants while being stored and/or while being deployed. In certain embodiments, the solid carrier comprises a solid at room temperature. In some embodiments, the solid carrier comprises a material that is frozen, but is liquid at room temperature. Different liquids may be utilized in frozen form. In certain instances, varying the liquid is useful for tuning the Raman interrogation results. Suitable liquids comprise alcohol, water, or the like.

In some embodiments, the solid projectile comprises a SERS-active materials (e.g., nanostructures comprising SERS-active materials) on the surface of the projectile. In certain embodiments wherein the projectile comprises SERS-active materials (e.g., nanostructures comprising SERS-active materials) on the surface thereof, the projectile comprises or is a retroflector. In some embodiments, this allows the Raman spectrometer to interrogate the projectile as it enters and/or while it is in the target area. In certain embodiments, wherein the projectile comprises or is a retroflector, the SERS-active materials on the surface thereof may or may not be in the form of nanostructures (i.e., in some embodiments, the SERS-active materials on the surface of the retroflector particle are not nano-structured).

In some embodiments, projectiles comprise SERS-active material and integrated optical elements to enhance the signal-to-noise ratio during stand-off interrogation. In a specific embodiments, a projectile comprising a SERS-active substrate in-line with a fiber-optic light guide to direct and restrict SERS interrogation to the SERS-active substrate. In certain embodiments, such a projectile may be reused. In some embodiments, such a projectile is removed following use and a new or recycled projectile of a similar type is attached to the fiber-optic light guide. In some embodiments, the telescopic optics includes a telescopic lens.

In some embodiments, the liquid projectile comprises SERS-active materials (e.g., nanostructures comprising SERS-active materials) and a liquid carrier. In certain embodiments, the liquid carrier is useful for protecting the SERS-active materials (e.g., nanostructures comprising SERS-active materials) from contaminants while being stored and/or while being deployed. In certain embodiments, the liquid projectile is deployed to the target area as a fluid stream (e.g., by pump), or is deployed to the target area as a particle (e.g., droplet). Different liquids may be utilized. In certain instances, varying the liquid is useful for tuning the Raman interrogation results. For example, depending on the analyte targeted, different liquids may be utilized (e.g., to potentially solubilize the analyte and condense with the analyte on the SERS-active surface). Suitable liquids comprise alcohol, water, or the like. In specific embodiments, the liquid is inert (e.g., substantially inert, particularly to the analyte being targeted).

In some embodiments, the SERS-active materials (e.g., nanostructures comprising SERS-active materials) comprise noble metals (e.g., nanostructured metallic power(s), including, e.g., nanoparticles), nanostructured granule(s) of SERS active materials (e.g., noble metallic granule(s), such as, nanoparticles or microparticles), nanostructured inorganic beads or other structures whose surfaces are coated with a SERS-active material or substrate (e.g., noble metallic nanoparticle(s) or nanostructure(s) or layers), inorganic beads (e.g., microstructured beads) whose surfaces are coated with a SERS-active material or substrate (e.g., noble metallic nanoparticle(s) or nanostructure(s) or layers), and any other suitable substrate(s).

In some embodiments, the device for deploying the deployable composition comprises a propulsion mechanism for deploying the projectile. In some embodiments, the propulsion mechanism is a spring-loaded propulsion device, a pressured gas propulsion device, a pump, or the like.

In certain embodiments, the Raman spectrometer comprises an interrogation laser and Raman sensor. The Raman sensor detects and measures vibrational signatures resulting from interrogation of SERS-active materials, or analytes deposited thereon. In certain embodiments, the laser is a collimated laser. In some embodiments, the Raman spectrometer is integrated with large-aperture telescopic optics. In certain embodiments, the Raman spectrometer is integrated with small-aperture telescopic optics.

In some embodiments, systems or devices described herein comprise multiple SERS-active material containing projectiles. In certain embodiments, such systems are multiple use systems and/or are long-term monitoring systems. In some embodiments, such multiple use or long-term monitoring systems comprise an automated configuration to incrementally deploy a SERS-active material containing projectile to a desired location and sample the air at the desired location. In certain instances, the automated configuration is a timer system, a system based on a triggering mechanism (e.g., opening a shipping container door within which the automated system is situated), or the like. In further or alternative embodiments, the multiple use and/or long-term monitoring system comprises a configuration to allow manual sampling of the air. Manual configurations may be independently or in combination with automated configurations.

In some embodiments, chemicals (e.g., unknown analytes or specifically targeted analytes) which are contained in the air are deposited on the SERS-active material. In certain embodiments, projectiles described herein comprise a liquid which evaporates upon deployment and facilitates deposition of the analyte on the SERS-active material.

Applications include chemical detectors for low-concentration analytes (such as those derived from drugs, explosives, and biological systems) and capable of both short-term, manually operated analysis, and long-term, automated monitoring and analysis.

In some embodiments, the analyte detection system further comprises at least one module configured to chemometrically process at least one output of the analyte detection system. In further or alternative embodiments, the system further comprises at least one module configured to adjust one or more variable operating parameters of the system (e.g., use of different projectiles, such as different projectiles comprising different liquids; length of interrogation; location of interrogation; or the like). In specific embodiments, at least one module is configured to adjust one or more variable operating parameters of the system is configured to adjust the one or more variable operating parameters based on the results of the chemometric processing of at least one output of the system.

As analytes interact with and/or are adsorbed or otherwise deposited onto SERS-active materials, they can be detected and/or analyzed using a variety of technologies. For example, the analytes may be studied using methods using various analytical instruments, such as one or more of a surface enhanced vibrational spectrometer, surface plasmon resonance spectrometer, a system based on electrochemical analysis techniques which may include molecular recognition elements, a system based on fluorescent chemical marker techniques, a system based on fluorescence quenching, a system based on redox-labeled nucleic acid binding techniques (including, but not limited to, the molecules DNA, RNA and PNA), a system based on X-Ray absorption techniques, IR spectrometer, visible analytical techniques, UV spectrometer, a system based on other electromagnetic radiation absorption techniques, mass spectrometer, a system based on liquid chromatography techniques, a system based on flame ionization analysis techniques, a system based on DNA melting point techniques, or a system based on titration analysis techniques. Further, the analytical instrument may be based on other analytical techniques utilizing chemical principles. In some embodiments, the analytical instrument is a Raman spectrometer (e.g., a Raman spectrometer suitable for surface-enhanced Raman spectroscopy (SERS)).

Various systems, devices, processes and approaches for detection and identification of low concentration gas-phase analytes have been developed and are set forth in co-pending applications, including WO 2009/020479, PCT/US10/34127, PCT/US10/45761, PCT/US10/52742, and U.S. 61/265,319, which are incorporated by reference in their entirety. In various embodiments, methods, components, devices, and systems described in these co-pending applications may be incorporated into the systems, devices and methods described herein.

BRIEF DESCRIPTION OF THE DRAWINGS

The foregoing features and other aspects of the invention are explained in the following description taken in conjunction with the accompanying figures. Further understanding of the features and advantages of the invention will be obtained by reference to the following detailed description that sets forth illustrative embodiments, in which the principles of the invention are utilized.

DETAILED DESCRIPTION OF INVENTION

Figure 1:
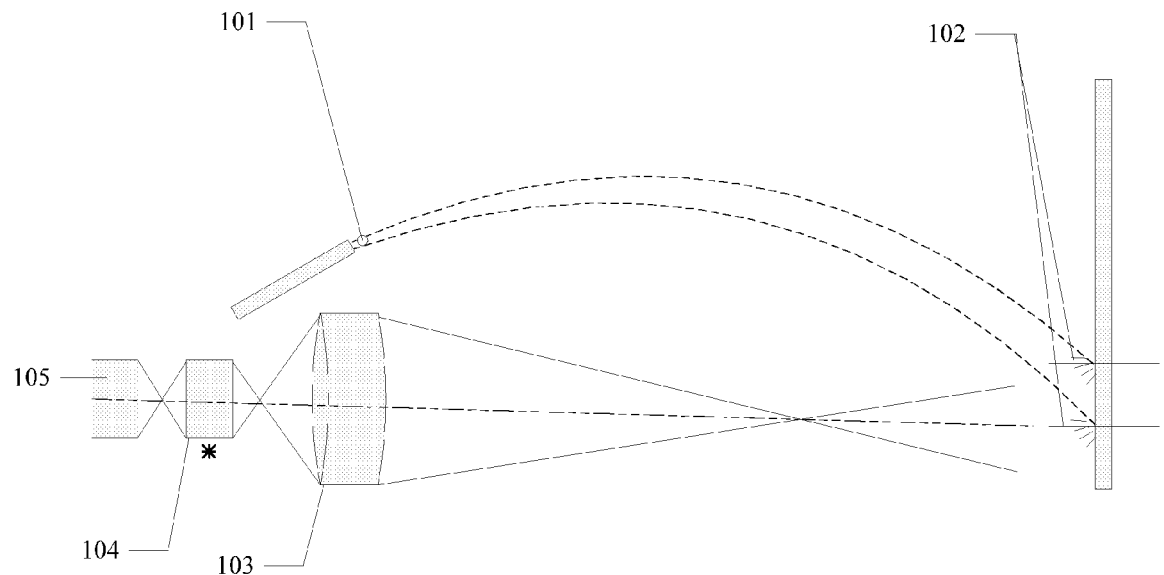
FIG. 1 illustrates an analyte detection system described herein.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The foregoing features and other aspects of the invention are explained in the following description taken in conjunction with the accompanying figures, wherein:

The detection and investigation of hazardous materials and explosives under field conditions presents multiple challenges: 1) how to conduct detection and analysis without hazarding human investigators; and, 2) how to conduct detection and analysis rapidly and accurately. Because certain applications—such as rapid deployments into and across threat zones—do not readily allow the use of robots and/or sophisticated approach methods due to time constraints, it is desirable that a system be both rapidly deployable and which allows for operation from a safe distance.

Applications of the present invention include chemical detectors for low-concentration analytes—such as those derived from drugs, explosives, and biological systems—and capable of both short-term and long-term analysis, which may be manual or automated.

Provided in certain embodiments herein is an optical system useful for interrogating SERS active materials (and detecting or measuring amounts of analytes deposited thereon) within test zones for the presence of analytes. In certain embodiments, such systems comprise an integrated telescopic optics and laser and, optionally, SERS active materials. In specific embodiments, optic systems described herein comprise, by way of non-limiting example: 1) an integrated, large-aperture telescopic optics and collimated laser; or, 2) integrated, scanning laser with small-aperture telescopic optics. SERS-active materials may be delivered to test zones or regions by any suitable mechanism including, by way of non-limiting example, one of the following methods:

a. In one embodiment, SERS-active materials are delivered to a test region in a liquid carrier, exposing the SERS-active materials to airborne analytes, b. In one embodiment, SERS-active materials are delivered to test regions via fragmentable projectiles, disbursing the enclosed SERS-active materials upon impact and rendering them airborne.

c. In one embodiment, SERS-active materials are delivered to test regions via fragmentable projectiles, disbursing the enclosed SERS-active materials upon impact and depositing them on fixed surfaces.

d. In one embodiment, SERS-active materials are delivered to a test region in an inert liquid carrier as a directed stream, exposing the SERS-active materials to airborne analytes, both enroute and upon impact e. In one embodiment, SERS-active materials are delivered to test sites via an inert liquid carrier which is frozen into solid pellet projectiles, disbursing the enclosed SERS-active materials upon impact and rendering them airborne. The physical properties of said pellets may be designed to control the degree of vaporization and other physical aspects of the frozen material after transformation into an airborne phase which is optimal for SERS detection of nearby airborne analytes.

f. In one embodiment, SERS-active materials are delivered to a test zone in an inert liquid carrier as a directed stream issuing from the exhaust nozzle of a fragmentable rocket, thus exposing the SERS-active materials to airborne analytes, both en route and upon impact.

g. In one embodiment projectiles in the form of retroreflective optical elements, having a partial or total outer coating of SERS-active materials, are launched into the test zone where said SERS-active materials interact with analytes. The retroreflective form of the projectiles serve to better direct the interrogating laser to the SERS-active surface of the optical elements, and boost the return signals, thus enhancing the optical gain of the system and reducing noise.

h. In one embodiment, projectiles, enclosing SERS-active substrates and interrogated via fiber-optic light guides, are launched into the test zone where they interact with analytes. The projectiles may take the form of wire-guided components. The wire guidance system may be used to transmit real-time spectroscopic or chemometric information from the projectile to another location. The wire guidance system may deploy light guides which span between a separate signal processing device or spectrometer and the projectile for the remote processing of light signals sampled from within or adjacent to the projectile during or after flight. The projectiles may be configured to enclose one or more SERS-active substrates that are in chemical, electrical, or optical communication with analyte-bearing fluids such as air or water, and to reduce or eliminate ambient environmental light, thus reducing optical noise and enhancing the optical interrogation signal for SERS readout of said substrates.

Projectiles described herein can be deployed to the test area in any manner. In certain embodiments, such projectiles may either be equipped with their own internal propulsion, or launched from a pressurized or sprung platform. In other embodiments, the projectiles may simply be deployed by hand, i.e., the projectiles may be hand-thrown projectiles. In the case of hand thrown projectiles attached to a fiber-optic light guide, such projectiles may simply be tethered by the fiber-optic light guides.

FIG. 1 illustrates one embodiment of the invention wherein a projectile containing SERS-active materials (101) is delivered to a test zone (102). In such embodiments, once reaching the test zone, the contents of the projectile, including the SERS-active materials, are disbursed upon impact. Once disbursed, the SERS-active materials are able to interact with analyte(s) within the zone. Other mechanisms that may be used to deliver the SERS-active materials include a liquid stream of inert fluid containing the SERS-active materials, frozen pellets of SERS-active material bearing fluid, or the like. Once the SERS-active materials have been deployed to the test zone, the SERS-active materials may be SERS-interrogated using an integrated laser (104) optionally with small- or large-aperture telescopic optics (103) and a sensor (105).

Figure 2:
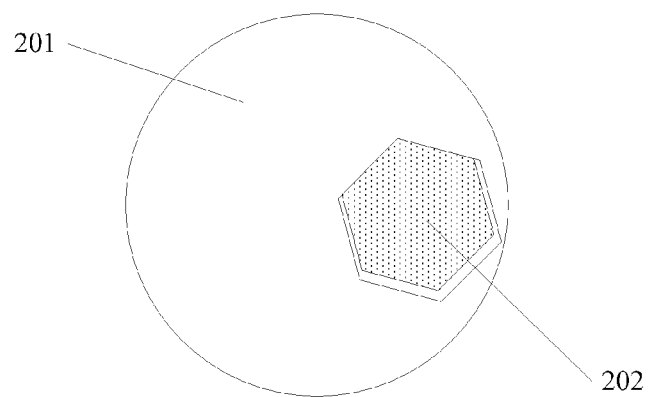
FIG. 2 illustrates a projectile entrapping nanostructures comprising SERS-active materials.

FIG. 2 illustrates one embodiment of the invention consisting of a sealed projectile (201) containing SERS-active materials (202). In certain embodiments, sealed projectiles are suitable for protecting SERS-active materials from contamination (e.g., during storage and/or deployment), and to fragment upon impact. Fragmentation upon impact of the projectile serves to expose the SERS-active contents to (potentially) analyte-bearing fluids within the test zone environment.

Figure 3:
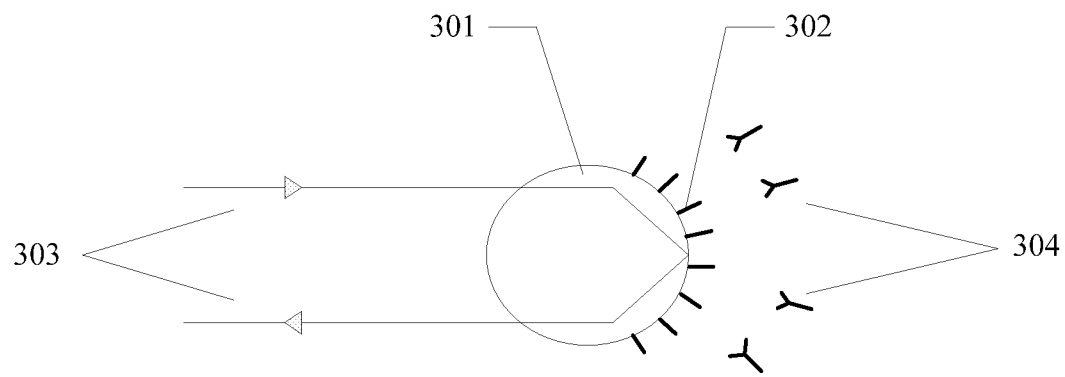
FIG. 3 illustrates a retroflector projectile.

FIG. 3 illustrates one embodiment of the invention wherein a projectile in the form of a retroreflective optical element (301) is coated with SERS-active materials (302). In certain embodiment, such projections may be deployed to the test zone and, once in the test zone, allow the SERS-active materials associated therewith to interact with analytes (304) within the test zone environment. The SERS-active materials may be optically interrogated from a remote location via the retroreflective optical path (303).

Figure 4:
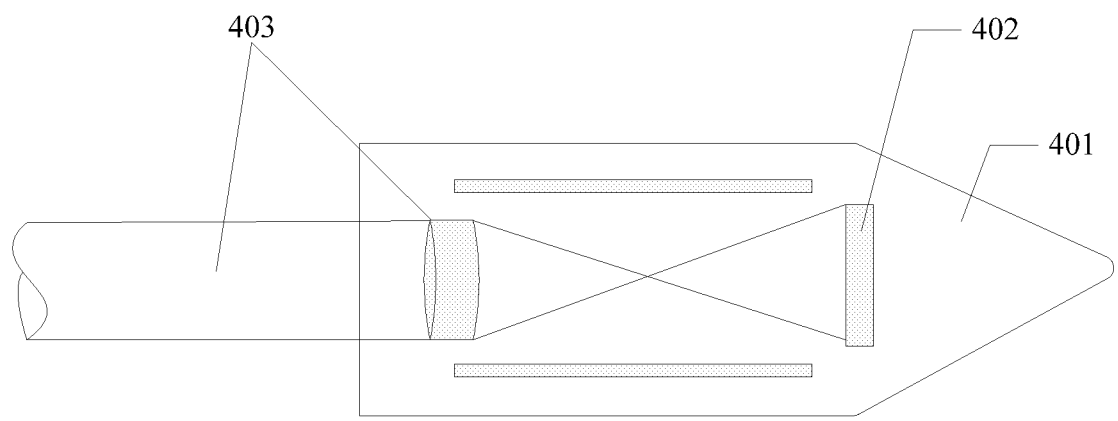
FIG. 4 illustrates a projectile comprising a SERS-active substrate in-line with a fiber-optic light guide.

FIG. 4 illustrates one embodiment of the invention wherein a projectile (401) which is partially or completely sealed. In certain embodiments, the projectile contains a SERS-active material or substrate (402) therein. The projectile, e.g., if completely sealed, may be unsealed en route the test zone, or upon impact within the test zone. Once within the test zone, the SERS-active material is exposed to analyte-bearing fluids (e.g., airborne analytes) within the test zone environment. A fiber-optic light guide (403) may be used to direct and restrict the SERS interrogation to the SERS-active substrate. In certain embodiments, use of a fiber-optic light guide may provide any one of a number of advantages, including, e.g., boosting optical gains and reducing noise due to ambient environmental light.

The invention claimed is:

1. An analyte detection system comprising
    a. a device for deploying a deployable composition to a location to be analyzed, the deployable composition comprising SERS-active sites; and
    b. a Raman spectrometer configured to allow interrogation of the SERS-active surface of the SERS-active material on an analyte adsorbed thereon, wherein Raman spectrometer includes telescopic optics, comprising a telescopic lens, and wherein the telescopic optics comprises a fiber-optics light guide.

2. An analyte detection system comprising:
    a. a device for deploying a deployable composition to a location to be analyzed, the deployable composition comprising SERS-active sites; and
    b. a Raman spectrometer configured to allow interrogation of the SERS-active surface of the SERS-active material on an analyte adsorbed thereon, wherein the deployable composition is a liquid composition comprising SERS-active sites and is deployable as a stream of SERS active sites in liquid.

3. An analyte detection system comprising:
    a. a device for deploying a deployable composition to a location to be analyzed, the deployable composition comprising SERS-active sites; and
    b. a Raman spectrometer configured to allow interrogation of the SERS-active surface of the SERS-active material on an analyte adsorbed thereon, wherein the deployable composition is a projectile comprising a SERS-active material and a liquid carrier.

* * * * *